United States Patent [19]

Bourgouin et al.

[11] Patent Number: 5,516,503
[45] Date of Patent: May 14, 1996

[54] DIAGNOSTIC COMPOSITION COMPRISING A BINUCLEAR COMPLEX, ITS METHOD OF PREPARATION AND ITS USE IN MAGNETIC RESONANCE IMAGING

[75] Inventors: Corinne Bourgouin, Paris; Gérard Desplanches, Boulogne; Michele Lecayon, Briis S/Forge, all of France

[73] Assignee: Guerbet S.A., Villepinte, France

[21] Appl. No.: 336,250

[22] Filed: Nov. 7, 1994

Related U.S. Application Data

[63] Continuation of Ser. No. 856,226, Jun. 18, 1992, abandoned.

[30] Foreign Application Priority Data

Nov. 16, 1989 [FR] France .................................. 89 15035

[51] Int. Cl.$^6$ ........................................................ A61B 5/055
[52] U.S. Cl. ........................ 424/9.364; 424/900; 514/186; 514/492; 514/502; 514/836; 436/173
[58] Field of Search .................. 424/9.364, 900; 514/186, 492, 502, 836; 534/16; 128/653.4, 654; 436/173

[56] References Cited

U.S. PATENT DOCUMENTS

| | | | |
|---|---|---|---|
| 5,039,512 | 8/1991 | Kraft et al. | 424/9 |
| 5,078,986 | 1/1992 | Bosworth et al. | 424/9 |
| 5,082,649 | 1/1992 | Van der Ripe | 424/9 |

FOREIGN PATENT DOCUMENTS

| | | |
|---|---|---|
| 0071564 | 2/1983 | European Pat. Off. . |
| 0133603 | 2/1985 | European Pat. Off. . |
| 0258616 | 3/1988 | European Pat. Off. . |
| 0263059 | 4/1988 | European Pat. Off. . |
| 2539996 | 8/1984 | France . |
| 2596992 | 10/1987 | France . |
| 8900052 | 1/1989 | WIPO . |

*Primary Examiner*—Gary E. Hollinden
*Attorney, Agent, or Firm*—Jacobson, Price, Holman & Stern

[57] ABSTRACT

A diagnostic composition comprising a binuclear complex between a polyaminopolycarboxylic ligand, such as diethylene triamine pentacetic acid, a paramagnetic metal such as Gd and an endogenous metal such as Ca, optionally mixed with the mononuclear complex of the same paramagnetic metal and the same ligand. This composition can be used as a contrasting agent in magnetic resonance imaging.

2 Claims, No Drawings

DIAGNOSTIC COMPOSITION COMPRISING A BINUCLEAR COMPLEX, ITS METHOD OF PREPARATION AND ITS USE IN MAGNETIC RESONANCE IMAGING

This is a continuation of application Ser. No. 07/856,226, filed Jun. 18, 1992, which is abandoned.

The present invention relates to a composition comprising a binuclear paramagnetic complex, usable for diagnostic purposes in particular as a contrast medium in magnetic resonance imaging (MRI) or as a chemical entrainer or as an agent with magnetic susceptibility.

Nuclear magnetic resonance spectroscopy (NMR) was developed in 1946 by Bloch and Purcell and this technique has since been widely used in the fields of physics, organic chemistry and biochemistry to study the chemical structure of molecules and of molecular groups "in vitro". The principle of NMR uses the conjunction of magnetic fields and radio-frequency waves to make the nuclei of certain atoms resonate. Since one of the most interesting atoms is hydrogen, which is present in the water which is the largest constituent of biological tissue (75 to 80% of soft tissue), it has been possible to envisage the use of the NMR technique in the field of medicine, and the development of nuclear magnetic resonance imaging in this field has made considerably rapid progress.

An image of the distribution of the protons is obtained from the signal emitted after the nuclei are made to resonate, and computer-aided reconstruction leads to the visualisation of transverse, sagittal and frontal sections through the human body.

To obtain the best results in MRI, contrast media have recently been developed allowing artificial accentuation of contrast by introducing, into the body to be examined, elements which notably modify the magnetic field, for example paramagnetic compounds, in order to perturb the relaxation times of the nuclei already present in the body, by adding, to the nuclear relaxation, a component linked with perturbations by an electronic magnetic moment.

The use of contrast media of this type is in particular described in the documents EP-A-0,071,564 (Schering A. G.), FR-A-2,596,992 (Guerbet S. A.) and WO-87/02893 (Board of Regents, the University of Texas System) but only the complexes consisting of the salt of di-N-methylglucamine (dimeglumine) of the complex Gd(III)-diethylenetriaminepentaacetic acid (DTPA) and the lysine salt of the complex Gd(III)-1,4,7,10-tetraazacyclodecane-N,N',N'',N''' tetraacetic acid (DOTA) have been developed respectively by Schering and Guerbet, and are used in hospitals.

In fact, the "in vivo" injection of paramagnetic complexes poses some problems of biological tolerance.

These problems which are due, in particular, to the possibilities of exchange between the paramagnetic element of the complex and the endogenous metals of the subject into which the complex has been injected, are expressed, on the one hand, by the "in vivo" liberation of the paramagnetic element, which is more or less toxic, of the complex injected and, on the other hand, by a depletion of the endogenous metal, for example of calcium or of zinc, of the subject.

To avoid these problems, two solutions have been proposed which consist:

- either in adding a calcium salt, that is to say an endogenous metal salt, to the complex solution injected in order to avoid the depletion of the endogenous metal, as is described in WO-89/00052,

- or in adding, to the paramagnetic complex solution, a complex formed between the same ligand and calcium in order to avoid the salting-out of the paramagnetic element, as is described in WO-9003804.

These two solutions are not however entirely satisfactory because the osmolality of the compounds remains high, these two additives not providing any improvement over the osmolality of the complex.

Now, as is indicated in Radiology 1988, 166, 897–899, the osmolality of the complex is a determining factor in the toxicity of the paramagnetic complexes.

Thus, the complex consisting of the di-N-methylglucamine salt of DTPA-Gd(III) has a high osmotic pressure (1940 mosm/kg according to the information of Berlex Lab. who market this product under the name Magnevist®); furthermore, its viscosity is significant and it must be used in high concentrations, generally in the form of a solution of 0.5 mol/l of complex. Also, its toxicity remains high.

The subject of the present invention is, precisely, a diagnostic composition usable in MRI which overcomes the disadvantages of the compounds described above.

The diagnostic composition according to the invention is characterised in that it comprises a binuclear complex between a cyclic or acyclic polyaminopolycarboxylic ligand, consisting of at least 6 electron donor atoms, a paramagnetic metal selected from lanthanides and the transition metals, and an endogenous metal selected from Ca, Mg, Zn, Cu, Co, Cr, Fe, Mn, V and Mo.

In the invention, binuclear, bimetallic or heteronuclear complex is understood to mean a complex in which the central element of the complex is formed from two different metals which are the paramagnetic element (lanthanide or transition metal) and the endogenous metal.

Such a binuclear complex behaves as a single particle and consequently has an osmolality weaker than that of a mononuclear complex formed between a paramagnetic element and a ligand consisting of at least 6 electron donor atoms.

Furthermore, with this binuclear complex, collection by the complex of the endogenous metals as well as the "in vivo" liberation of the toxic paramagnetic element are limited at the time of "in vivo" injection.

In fact, the exchange of an endogenous metal from the subject occurs "as a priority" with the endogenous metal present in the central element of the binuclear complex.

Thus, the use of such a binuclear complex in the diagnostic composition of the invention allows the difficulties of the known solutions to be overcome and also the osmolality of the solution injected to be reduced.

According to a preferred embodiment of the invention, the diagnostic composition comprises a mixture of the said binuclear complex and a mononuclear complex between the same ligand and the same paramagnetic metal.

In this mixture, the molar ratio of the mononuclear complex to the binuclear complex can be from 0.1 to 1.

Such a mixture even with a 1:1 ratio allows sufficient reduction in the osmolality and the toxicity of the diagnostic compound to render it more suitable for "in vivo" injection and to facilitate its use as a contrast medium or as a chemical shift reagent or as an agent with magnetic susceptibility in MRI.

In the invention, the paramagnetic metal may be selected from the lanthanides and the transition metals. For example, gadolinium, manganese, iron or copper may be used in the compounds to be used as a contrast medium.

In the case where the composition is to be used as a chemical shift reagent or as an agent with magnetic susceptibility, it is preferable to use Tm, Tb, Gd, Eu, Dy, Ho or Er as the paramagnetic metal.

The endogenous metals used are those which are generally present in trace quantities but constitute elements which are essential to the human body. Preferably Ca, Zn or Cu are used.

The polyaminopolycarboxylic ligands used in the invention must comprise at least 6 electron donor atoms and can be cyclic or acyclic ligands.

Among these ligands, the aminocarboxylic acids such as those described in EP-A-0071564 may be mentioned in particular, for example diethylenetriaminepentaacetic acid (DTPA), triethylenetetraaminehexaacetic acid (TTHA), trans-1,2-diaminohexanetetraacetic acid (CYDTA) and the tetraaza- or diazamacrocyclic compounds like 1,4,7,10-tetraazacyclododecane-N,N',N",N"'-tetraacetic acid (DOTA). The ligand may also be coupled to a biological molecule such as a monoclonal antibody.

The diagnostic composition of the invention may be in particular in the form of an aqueous solution containing the binuclear complex, possibly mixed with the mononuclear complex.

The aqueous solution is a physiologically acceptable solution which may comprise other pharmaceutically acceptable additives such as stabilisers, if necessary.

In general, the solution comprises from 0.2 mol/l to 1.2 mol/l in total of complex(es) of the paramagnetic metal.

The compounds of the invention can easily be prepared starting from a compound of the paramagnetic metal, for example an oxide or a chloride, from the appropriate ligand, from a salt of the endogenous metal and possibly from an organic base such as the basic amino acids and N-methylglucamine.

In addition, also within the scope of the invention is a method of preparation of such a composition, which comprises the following stages:

a) preparation of a mononuclear complex between a polyaminopolycarboxylic ligand, consisting of at least 6 electron donor atoms and a paramagnetic metal, by reaction of a compound of the paramagnetic metal with the polyaminopolycarboxlic ligand, b) preparation of a binuclear complex of the same paramagnetic metal, of an endogenous metal and of the same polyaminopolycarboxylic ligand by reaction of a compound of the paramagnetic metal with the ligand and a salt of the endogenous metal, and c) preparation of an aqueous solution of the mononuclear complex obtained in stage a) and of the binuclear complex obtained in stage b).

In some cases, in particular when the complexes formed have negative charges, a complementary neutralisation stage is carried out by addition to the aqueous solution obtained in stage c) of an organic base chosen from among the basic amino acids and N-methylglucamine.

By way of example of usable amino acids, lysine and arginine may be mentioned.

Preferably, in stage c), the molecular ratio of the mononuclear complex/binuclear complex is from 0.1 to 1.

For the implementation of this method, salts or oxides of the paramagnetic metals in stages a) and b) may be used. In stage b) the salt of the endogenous metal used may be, for example, a carbonate.

The diagnostic compositions of the invention which may be administered to man may be used in particular as a contrast medium in magnetic resonance imaging (MRI).

They may also be used as chemical shift reagent or as agents with magnetic susceptibility in magnetic resonance imaging, as is described in Mag Res in Med. 6, 164–174, 1988. In this case, the paramagnetic metal is preferably Tm, Tb, Gd, Eu, Dy, Ho or Er.

The diagnostic compositions of the invention may be administered to man parenterally (in particular by the vascular or lymphatic routes), sub-arachnoidally, orally or intrabronchially.

For parenteral or oral administration, the composition is preferably made up of a solution of the binuclear complex or of a mixture of mono- and binuclear complexes in a physiologically acceptable aqueous solvent which preferably contains from 0.2 to 1.2 mol/l of paramagnetic complex(es), for example 0.5 mol/l.

The solution contains in particular 0.8 mol/l of the complexes and the administrable dose is in general from 0.05 to 5 mmol/kg of body weight, for example 0.1 mmol/kg.

The invention will be better understood by reading the following description, which is given, of course, by way of example and is not limiting, which deals with the preparation and the properties of the diagnostic composition according to the invention and comprising a mixture of a mononuclear complex (Gd) and a binuclear complex (Gd-Ca).

I. Preparation of the Diagnostic Composition a) Preparation of the mononuclear complex Gd-DTPA 100 g (0.275 mol) of gadolinium oxide $Gd_2O_3$ and 217 g (0.55 mol) of diethylenetriaminepentaacetic acid (DTPA) are dissolved in 2 l of water for injectable preparations (ppi). Heating under reflux is carried out until the products have completely dissolved, the solution is filtered and the volume of solution collected is measured accurately in order to calculate the concentration of $H_2Gd \cdot DTPA$ complex. This concentration is of 0.44 mol/l.

b) Preparation of the binuclear complex Ca-Gd(III)-DTPA 100 g (0.275 mol) of gadolinium oxide $Gd_2O_3$ and 217 g (0.55 mol) of diethylenetriaminepentaacetic acid (DTPA) are dissolved in 2 l of water (ppi), heating under reflux is carried out until the products have completely dissolved, the solution is filtered, and the filtrate is heated while adding 55.23 g (0.55 mol) of calcium carbonate ($CaCO_3$). The volume of the solution is reduced by ¼ through heating. The precipitate is collected and dried under vacuum, then it is redissolved in 2 l of water (ppi), the volume of the solution is reduced by ¼ through heating, the precipitate is collected and is dried under vacuum.

In this way 279.6 g (0.477 mol) of Ca-Gd-DTPA are obtained.

c) Preparation of the aqueous solution of the complexes Gd-DTPA and Ca-Gd-DTPA 1074 ml of the solution of $H_2Gd$-DTPA obtained in a) are mixed with 1311 ml of water, then 279.6 g of the Ca-Gd-DTPA complex obtained in stage b) are dissolved in the solution obtained and the solution is mixed until the product has completely dissolved.

d) Neutralisation

The pH of the solution obtained in stage c) is adjusted to 7 by adding 150 g of N-methylglucamine.

In this way, a solution of Gd-DTPA and Gd-Ca-DTPA is obtained.

The solution is then sterilised by filtration and is placed in flasks, in an amount of 20 ml per flask, while carrying out this operation in a sterile enclosure.

II. Formulation of the Complex Solution

Complexes content per 20-ml flask: 6.08g content per ml: 0,304 g gadolinium content per 20-ml flask: 1.26 g content per ml: 0.063 g calcium content per 20-ml flask: 0.16 g content per ml: 0.008 g diethylenetriaminepentaacetic acid (DTPA)

content per 20-ml flask: 3.10 g content per ml: 0.155 g

N-methylglucamine content per 20-ml flask: 1.56 g content per ml: 0.078 g.

The physicochemical characteristics of the solution, its stability, its acute toxicity, its capacity for bonding with plasmatic proteins and the relaxation times $T_1$ and $T_2$ in different bodies are given hereinbelow.

1. Physicochemical Characteristics

Osmolality determined by means of an osmometer by the technique in propharmacopoea 360, Ordre National des Pharmaciens no. 293, June 1986 : osmolality=812 mosm/kg at 37° C.

Viscosity determined by means of a capillary tube according to the standards of the French pharmacopoeia:

viscosity=0.096 cPas.

2. Stability of the Composition

This stability has been studied in a sanguinary medium by following the development of the concentration of free gadolinium and of free calcium by paper chromatography with the complexes of the invention marked with gadolinium 153 and with Ca 47.

The results obtained are given in Table 1 which follows.

TABLE 1

| Stability of the DTPA-Gd-Ca complex (meglumine) | | | | |
|---|---|---|---|---|
| COMPLEX | BLOOD | | GLUCOSE | |
| SOLUTION | Plasma | Erythrocytes | SOLUTION | URINE |
| $^{153}$Gd, complexed | 99.05% | $^{153}$Gd fixed by erythrocytes | | |
| $^{153}$Gd, free | 0.95% | 0.001% | 0.85% | <2.5 × $10^{-3}$ g/l |
| $^{47}$Ca, complexed | 98.9% | $^{47}$Ca fixed by erthrocytes | | |
| $^{47}$Ca, free | 0.4% | 0.7% | 6.4% | |

Gd and Ca remain complexed in solution in plasma in the presence of erythrocytes.

The presence of free gadolinium in urine is also tested "in vivo". A green coloration is obtained for all the urine samples and colorimetry does not show free gadolinium, the content of free gadolinium being less than $2.5 \times 10^{-8}$ g/l.

3. Acute Toxicity of the Composition of the Invention

The acute toxicity of the composition is tested in male mice by a single intravenous injection in 1 min, using the method of Bliss. The results obtained are as follows:

LD50=3760.6 mg/kg (5.02 mmol/kg).

This value is greater than that obtained with the DTPA-Gd-dimeglumine complex of document FR-A-2 596 992 (4.45 mmol/kg). Thus, the composition of the invention is less toxic.

4. Capacity for Bonding with Plasmatic Proteins

Bonding with proteins is not observed in plasma for the complexes of the invention tested by using gadolinium 153 chloride as a reference.

5. Evaluation of the Relaxation Times T1 and T2 in the Body

For this determination, male rats of the Wistar strain weighing about 250 g are used and half of the rats are injected with a urea solution of 3 mol/l into the right carotid to disrupt the blood-brain barrier (BBB), then, intravenously, with the composition of the invention corresponding to the formulation described in II at a dose of 2 ml/kg.

1 minute later, the rats are killed, their brains are removed and the relaxation times T1 and T2 in the left hemisphere, the right hemisphere and the cerebellum are determined.

The longitudinal relaxation time T1 (spin-lattice) is linked to the creation of the longitudinal magnetisation oriented along the magnetic field $B_0$ and is determined by the energetic relationships between the nuclei and the lattice.

The transverse relaxation time T2 (spin-spin) is defined by the return to equilibrium, in magnitude and in direction, of the longitudinal magnetisation (parallel to B0) which has been negated or modified by the radio-frequency pulse. It is also expressed by the return to zero of the transverse magnetisation which has been created by the radio-frequency pulse.

The results obtained are given in the attached Table 2.

These results show that from 1 min to 30 min after injection, the relaxation times T1 and T2 are shortened, which proves that the contrast medium is effective.

Thus, in relation to the Gd-DTPA-dimeglumine complex, the advantages of the composition of the invention are as follows:

a lower osmotic pressure, a lower viscosity, a lower toxicity, and the possibility of being used at a lower concentration.

Moreover, it has a very great stability due to the calcium complexing.

In fact, the composition of the invention comprises less free DTPA than the Gd-DTPA-dimeglumine complex of Shering, which can collect calcium in the blood, thus producing a demineralisation due to the free DTPA.

In the case of the invention, the binuclear complex, which already contains complexed calcium, will not complex the calcium of the body.

In the same manner, the binuclear DTPA-Gd-Zn complex may be obtained.

TABLE 2

RELAXATION TIMES IN THE BRAIN

|  | Healthy animal without injection of contrast medium | BBB-disrupted animal, sacrificed 1 minute after injection of DTPA-Gd-Ca (meglumine) | |
|---|---|---|---|
|  | Milliseconds | Milliseconds | % reduction |
| T1 Left hemisphere | 629.32ms | 344.42ms | 45.2 |
| Right hemisphere | 689.72ms | 302.32ms | 56.2 |
| Cerebellum | 655.78ms | 291.04ms | 55.6 |
| T2 Left hemisphere | 81.75ms | 70.05ms | 14.4 |
| Right hemisphere | 81.63ms | 65.72ms | 19.5 |
| Cerebellum | 88.60ms | 69.70ms | 21.6 |

We claim:

1. A process for preparing a MRI composition including, (i) a mononuclear complex of diethylene triamine pentaacetic acid (DTPA) with gadolinium ion ($Gd^{3+}$), and (ii) a binuclear complex of DTPA with $Gd^{3+}$ and an endogenous metal ion which is $Ca^{2+}$, comprising the steps of:

(a) preparing the mononuclear complex Gd-DTPA by reacting DTPA with $Gd_2O_3$;

(b) preparing the binuclear complex Ca Gd-DTPA by reacting the mononuclear complex obtained in step (a) with $CaCO_3$;

(c) combining selected amounts of the mononuclear complex with the binuclear complex in an aqueous solution; and (d) neutralizing the solution obtained in step (c) with an organic base selected from the group consisting of a basic aminoacid and N-methylglucamine.

2. A process for preparing a MRI composition including (i) a mononuclear complex of diethylene triamine pentaacetic acid (DTPA) with gadolinium ion ($Gd^{3+}$), and (ii) a binuclear complex of DTPA with $Gd^{3+}$ and an endogenous metal ion which is $Ca^{2+}$, comprising the steps of:

(a) preparing the mononuclear complex Gd-DTPA by reacting DTPA with $Gd_2O_3$;

(b) preparing the binuclear complex Ca Gd-DTPA by reacting the mononuclear complex obtained in step (a) with $CaCo_3$;

(c) combining, at a molar ratio of 0.1 to 1, the mononuclear complex with the binuclear complex in an aqueous solution; and (d) neutralizing the solution obtained in step (c) with an organic base selected from the group consisting of a basic aminoacid and N-methylglucamine.

* * * * *